United States Patent [19]

Haber

[11] Patent Number: 4,846,784
[45] Date of Patent: Jul. 11, 1989

[54] MANUALLY ADJUSTABLE SPHINCTERIC SYSTEM

[75] Inventor: Terry M. Haber, Lake Forest, Calif.

[73] Assignee: C. R. Bard, Inc., Murray Hill, N.J.

[21] Appl. No.: 68,555

[22] Filed: Jul. 1, 1987

[51] Int. Cl.⁴ ............................................. A61B 19/00
[52] U.S. Cl. .............................. 600/29; 128/DIG. 25
[58] Field of Search ....................... 128/1 R, DIG. 25; 604/256; 600/29

[56] References Cited

U.S. PATENT DOCUMENTS

| | | | |
|---|---|---|---|
| 3,841,304 | 10/1974 | Jones | 128/DIG. 25 |
| 3,854,469 | 12/1974 | Giori et al. | 128/DIG. 25 |
| 3,903,894 | 9/1975 | Rosen et al. | 128/DIG. 25 |
| 4,217,889 | 8/1980 | Radovan et al. | 128/1 R |
| 4,552,128 | 11/1985 | Haber | 128/DIG. 25 |
| 4,587,954 | 5/1986 | Haber | 128/1 R |
| 4,610,665 | 10/1986 | Matsumoto et al. | 604/256 |
| 4,619,245 | 10/1986 | Haber et al. | 128/DIG. 25 |
| 4,634,443 | 1/1987 | Haber | 128/1 R |
| 4,643,733 | 2/1987 | Becker | 128/1 R |
| 4,673,393 | 6/1987 | Suzuki et al. | 604/256 |
| 4,690,375 | 9/1987 | Uorhis | 604/256 |
| 4,692,152 | 9/1987 | Embe | 604/265 |

OTHER PUBLICATIONS

Implantable Artificial Sphincter, K. Affeld Kintzonidis, Vol. XVII, Trans. Amer. Soc. Artif, Int. Organs, 1971.

Primary Examiner—John D. Yasko
Attorney, Agent, or Firm—Morland C. Fischer

[57] ABSTRACT

An active, as opposed to a passive, sphincteric system to be implanted within or near the periurethral tissues of an incontinent patient. The system includes a genitourinary prosthesis comprising an inflatable (and deflatable) balloon (rather than a cuff) which is percutaneously infused with and inflated by a supply of hydraulic fluid or suspended particulate matter to increase both the localized tissue density proximal to the urethra and the passive occlusive pressure applied to the urethra for returning the patient to continence. The system includes an accumulator or reservoir and a check valve located between the accumulator and the balloon to control the flow of fluid or suspended particles therebetween. The check valve may be manually opened, whereby the balloon shrinks and the accumulator swells. Subsequently, the accumulator may be manually compressed, whereby fluid or suspended particles are transferred back to the balloon, by hydrostatic pressure, to reinflate the balloon. Positioning and inflating instrumentation is also disclosed by which to implant the sphincteric system according to a relatively simple insertion process.

18 Claims, 4 Drawing Sheets

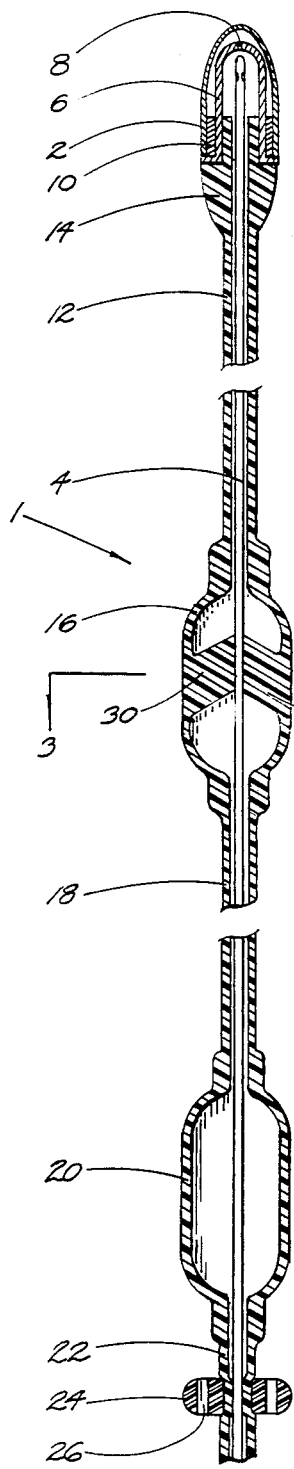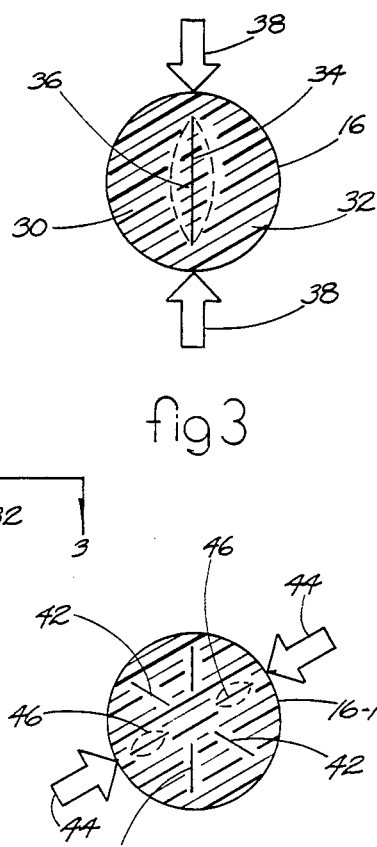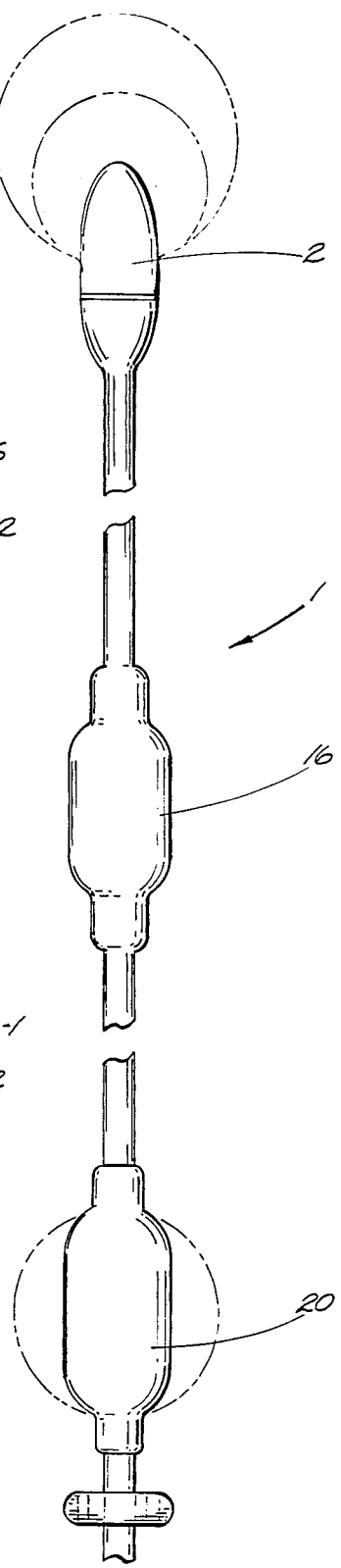
fig 1  fig 3  fig 4  fig 2

MANUALLY ADJUSTABLE SPHINCTERIC SYSTEM

BACKGROUND OF THE INVENTION
1. FIELD OF THE INVENTION

This invention relates to an active, manually adjustable sphincteric system for the treatment of incontinence and to positioning and inflating instrumentation by which to implant the sphincteric system according to a relatively simple insertion process.

2. PRIOR ART

In each of U.S. patent application Nos. 881,829; 881,830; and 882,086, all of which being filed on July 3, 1986, there is disclosed a unique, genitourinary prosthesis comprising an expandable, inflatable anti-migration membrane which is periurethrally injected between the urethra and the corpus spongiousum of a patient to be percutaneously infused with fluid or suspended particulate matter so as to overcome urinary incontinence by means of a controlled increase of localized tissued density. The inflatable membrane functions as a containment envelope for retaining the fluid or particles therewithin and preventing the undesirable migration of such particles from the injection site. Accordingly, an increased passive occlusive pressure may be applied to the patient's urethra for returning the patient to continence while avoiding the possible health hazards that might otherwise be encountered should the fluid or suspended particles be permitted to migrate from the injection site.

However, the inflatable membranes described in each of the above-identified patent applications represent passive sphincteric systems. That is to say, once the membrane is implanted and inflated, the patient can do little to either control or vary the amount of occlusive pressure being applied by the membrane to his urethra. An overly inflated membrane may produce excessive levels of occlusive pressure and, consequently, require additional surgery for either explant or adjustment of such membrane. Accordingly, it would be desirable to include the inflatable membrane as an integral part of an active sphincteric system by which to enable the patient to manually and selectively control the inflation/deflation of the membrane and the level of occlusive pressure generated thereby.

SUMMARY OF THE INVENTION

Briefly, an active, implantable, manually adjustable sphincteric system is disclosed for the treatment of incontinence. The system includes a genitourinary prosthesis comprising a normally uninflated balloon (rather than a cuff) which is adapted to be inflated (or deflated) with and provide an anti-migration enclosure for a supply of hydraulic fluid or suspended particulate matter. The balloon is preferably located at the bulbar urethra, such that an inflation of the baloon proportionately increases local tissue density in the areas of the corpus spongiousum to correspondingly increase the occlusive pressure applied to the urethral tissues for returing a patient to continence.

The sphincteric system includes an inflatable, manually activatable hydraulic accumulator which is implanted below a palpable, loose skin area of the patient. The accumulator communicates with the balloon to receive fluid or suspended particles therefrom when the balloon is deflated and the occlusive pressure applied to the urethral tissues is correspondingly reduced. What is more, by manually applying equal and opposite compressive forces to the accumulator, fluid or particles can be supplied, by hydrostatic pressure, from the accumulator to the balloon to reinflate the balloon and restore the patient to continence.

The sphincteric system further includes a flow control check valve which is also implanted below a palpable, loose skin area of the patient between the balloon and the accumulator to control the transfer of fluid or particle therebetween. The check valve is normally biased to permit fluid or particles to be supplied from the accumulator to the balloon, whereby to prevent an unintentional deflation of the balloon and a loss of continence. However, by manually applying equally and opposite compressive forces against opposing pressure surfaces of the check valve, fluid or particles may be selectively transferred from the balloon to the accumulator to controllably deflate the balloon.

A simple, knottable filling and sealing valve is provided to permit fluid infusion into and fluid sealing of the balloon. An elongated cannula is moved through the filling and sealing valve and is extended between a source of fluid or suspended particulate matter and the balloon, so that the balloon can be percutaneously infused with and inflated by a supply of such fluid or particles. Once the balloon has been inflated, the cannula is removed.

The sphincteric system is implanted by means of an inner and outer trocar assembly which is adapted to pierce a small insertion channel or tunnel through the periurethral tissues, whereby to minimize both trauma and tissue loss. The outer trocar tube also serves as a guide and protective casing for accurately positioning the balloon (in an uninflated condition) at the target site within the patient's tissues.

BRIEF DESCRIPTION OF THE DRAWINGS

FIG. 1 is a cross-section of the sphincteric system which forms the present invention;

FIG. 2 is representative of a reciprocal filling and emptying system which is characteristic of the sphincteric system of FIG. 1;

FIG. 3 is a cross-section taken along lines 3—3 of FIG. 1 illustrating a check valve of the present sphincteric system;

FIG. 4 is a cross-section showing an alternative check valve;

DESCRIPTION OF THE PREFERRED EMBODIMENT

Figure 5:
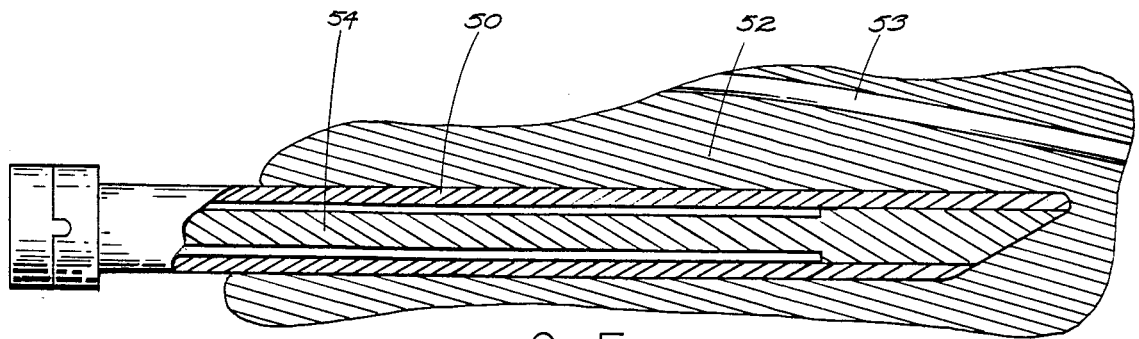
FIGS. 5 and 6 show cross-sections of an inner and outer trocar assembly for piercing a channel through the periurethral tissues, so that the present sphincteric system can be implanted.

The active, manually adjustable sphincter which forms the present invention is now described while referring to the drawings, where in FIG. 1 there is shown a sphincteric system 1 including an implantable genitourinary prosthesis and an associated fluid control circuit. The genitourinary prosthesis of sphincteric system 1 comprises an inflatable occlusion membrane or balloon 2. Occlusion balloon 2 is preferably formed from a suitable tear-resistant, biocompatible material, such as, for example, polyurethane, silicone, latex, or the like. Extending longitudinally through the sphincteric system 1 is a hollow cannula 4 which, as will be disclosed in greater detail hereinafter, communicates with a source of supply of hydraulic fluid or suspended particulate matter (e.g. a hypodermic syringe) to supply fluid or suspended particles for inflating the occlusion balloon 2. Accordingly, balloon 2 also serves as an anti-migration enclosure in which to contain the fluid or particles delivered by cannula 4.

A hemispheric, plastic or metal safety shield 6 is located between the fluid delivering distal end of cannula 4 and the occlusion balloon 2. Safety shield 6 prevents the cannula 4 from accidentally penetrating the occlusion balloon 2, whereby to avoid the possibility of leaking migratory fluid or particulate matter into the patient's body. Safety shield 6 is also provided with one or more delivery ports 8 extending therethrough. The delivery ports 8 permit communication between the cannula 4 and the interior of the ooclusion balloon 2 during the inflation of the balloon. Adjacent ends of the saftey shield 6 and the occlusion balloon 2 are secured to one another by means of a vulcanized silicon bond layer 10, or the like.

The fluid control circuit of sphincteric system 1 is preferably fabricated from a biocompatible material, such as silicone, or the like, and includes a distal tubing section 12 which extends between an end plug 14 and a manually assessible and manually activatable fluid control check valve 16. End plug 14 supports and maintains the occlusion balloon 2, the distal, fluid delivering end of cannula 4, and safety shield 6 in coaxial alignment with one another. Check valve 16 will be described in greater detail when referring to FIGS. 3 and 4. A medial tubing section 18 extends between check valve 16 and an inflatable, relatively thin walled, manually accessible and manually activatable accumulator or reservoir 20. As is depicted in FIG. 2 of the drawings, accumulator 20 forms a reciprocal filling and emptying system with occlusion balloon 2. That is to say, accumulator 20 (which is shown in its normally relaxed condition in FIG. 1) will be emptied via check valve 16 when the occlusion balloon 2 is inflated, and accumulator 20 will be fitted via check valve 16 when the occlusion balloon 2 is deflated.

Referring once again to FIG. 1, a proximal tubing section 22 extends between accumulator 20 and a hypodermically accessible infusion port (not shown) at which the fluid circuit of sphincteric system 1 is infused with a supply of fluid or particulate matter by way of a hypodermic syringe (also not shown). A removable O-ring 24 surround proximal tubing section 22 to apply sufficient occlusive forces thereagainst to form a filling and sealing valve and prevent any leakage or backflow of fluid or particulate matter during the filling of the fluid circuit and the inflating of the occlusion balloon 2. O-ring 24 includes an access opening 26 at which a tool (e.g. a hemostat) may grasp and remove the O-ring after the sphincteric system 1 is properly filled and inflated.

FIGS. 3 and 4 of the drawings provide examples for implementing the check valve 16 of FIG. 1. In FIG. 3, the check valve 16 includes a hollow cylindrical body having a pair of oppositely aligned and laterally extending lobes 30 and 32. A normally closed, narrow slit 34 is created at the interface of the lobes 30 and 32. Slit 34 will be automatically opened by hydrostatic pressure in response to fluid flow from the accumulator 20 to the occlusion balloon 2. However, slit 34 will remain closed in response to fluid backflow from the balloon 2 to the accumulator 20 to prevent an unintended deflation of the balloon. Nevertheless, the patient can manually open the check valve 16 whereby to separate the lobes 30 and 32 so as to create a fluid passage 36 therebetween. By applying equal and opposite forces (represented by reference arrows 38) to the check valve 16 at a pair of opposing pressure surfaces which coincide with the longitudinal axis of slit 34, the lobes 30 and 32 can be separated from one another so that slit 34 will be opened to permit fluid to flow through the passage 36 from an inflated balloon 2 to the accumulator 30 for a purpose that will be better understood when referring hereinafter to FIG. 12.

In FIG. 4, an alternate check valve 16-1 is shown. Instead of a single, continuous slit (like that designated 34 in FIG. 3), check valves 16-1 is characterized by (e.g. six) pairs of non-intersecting and non-continuous slits 42. Each slit of a pair of the slits 42 is longitudinally aligned with but separated from the second of the pair of slits at the center of the check valve 16-1. The patient may manually open any pair of slits 42 so as to create respective fluid passages 46 therethrough by applying equal and opposite compressive forces (represented by reference arrows 44) to the check valve 16-1 at any corresponding pair of opposing pressure surfaces which coincide with the longitudinal axes of such pair of slits. Thus, it will be easier for a patient to open the check valve 16-1 so as to permit fluid to be transferred from an inflated balloon 2 to the accumulator 20.

Positioning and inflating apparatus and a relatively simple technique for perineally implanting the sphincteric system 1 of FIG. 1 are now described while referring to FIGS. 5-13 of the drawings. In FIG. 5, an outer trocar tube 50 is provided to pierce the periurethral tissues 52 of the patient to establish a suitable channel or tunnel therethrough, so that the sphincteric system may be implanted. To this end, outer trocar tube 50 is provided with a sharp, oblique cutting surface for establishing the channel or tunnel through the periurethral tissues by which to insert sphincteric system 1. The trocar tube 50 is preferably formed from a bicompatible and corrosion-resistant material, such as titanium, or the like. As will soon be described, outer trocar tube 50 also functions as a protective casing and guide for precisely locating the occlusion balloon (designated 2 in FIG. 1) relative to the patient's urethra 53. By way of specific example, occlusion balloon 2 of the sphincteric system 1 may be implanted within the bulbar urethra of the corpus spongiousum.

Prior to the step of penetrating the periurethral tissues 52, a non-coring inner trocar rod 54 of solid cross-section is inserted in and completely through the hollow trocar tube 50. Inner trocar rod 54 is formed of stainless steel, or the like, and has a closed oblique end to prevent the patient's tissue from entering outer tube 50 during such time as when the outer trocar is used to penetrate the urethral tissues 52. Hence, trauma will be minimized, because none of the patient's tissues will be removed with the outer trocar tube 50 at the conclusion of the implanting process.

Figure 6:
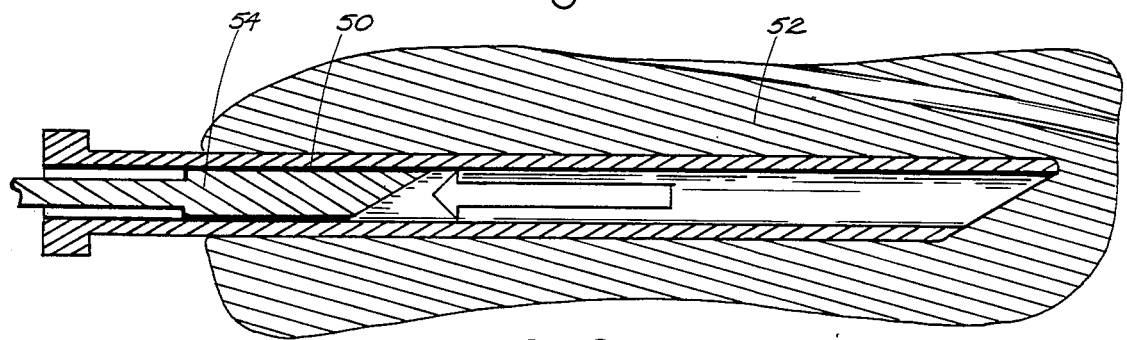

Once a suitable channel or tunnel has been pierced by the outer trocar tube through the patient's periurethral tissues 52, the inner trocar rod 54 is withdrawn from outer tube 50 (best depicted in FIG. 6). Another example of utilizing a combination outer trocar tube and non-coring inner trocar rod for implanting an inflatable genitourinary prosthesis may be found by referring to U.S. patent application Ser. No. 881,829 filed July 3, 1986 by Terry M. Haber, et al.

Figure 7:
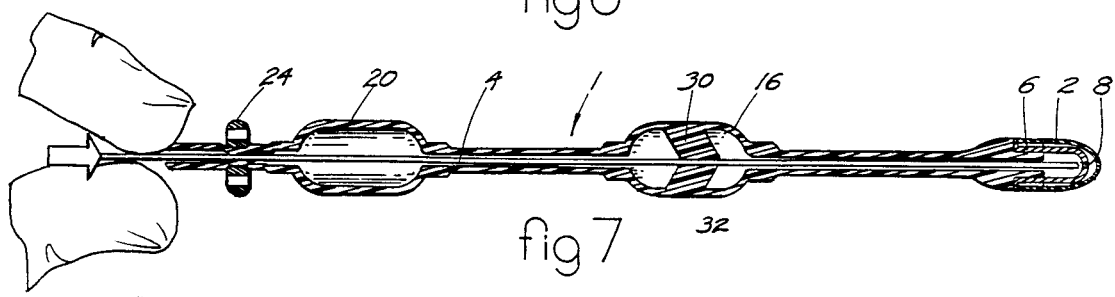
FIG. 7 shows the insertion of an elongated cannula through the present sphincteric system for communication with an inflatable balloon.

In FIG. 7, the physician grasps the hollow cannula 4 at the proximal end thereof and inserts the cannula through the sphincteric system 1 until the distal fluid delivering end of cannula 4 is received within the safety shield 6 at the interior of occlusion balloon 2. As previously indicated, the safety shield 6 prevents an accidental puncture of the balloon by cannula 4 when such cannula is moved distally through sphincteric system 1. In FIG. 7, the cannula 4 is shown extending past the constriction formed by O-ring 24, through the accumulator 20, and between the lobes 30 and 32 of check valve 16, so as to deliver fluid or suspended particulate matter from a source thereof to the occlusion balloon 2 via the delivery port 8 in safety shield 6.

Figure 8:
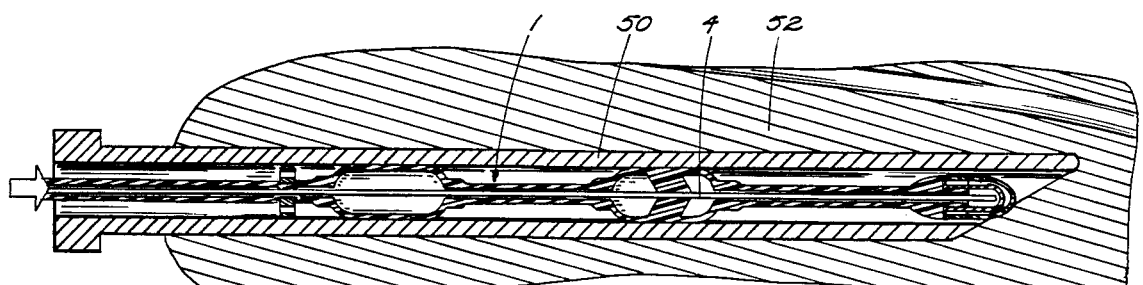
FIG. 8–11 illustrate the steps for locating and inflating the inflatable balloon of the present sphincteric system.

In FIG. 8, the sphincteric system 1 and cannula 4 of FIG. 7 are inserted into and through the outer trocar tube 50 after a channel has been pierced through the patient's periurethral tissues and the inner trocar rod (designated 54 in FIG. 5) has been removed.

Figure 9:
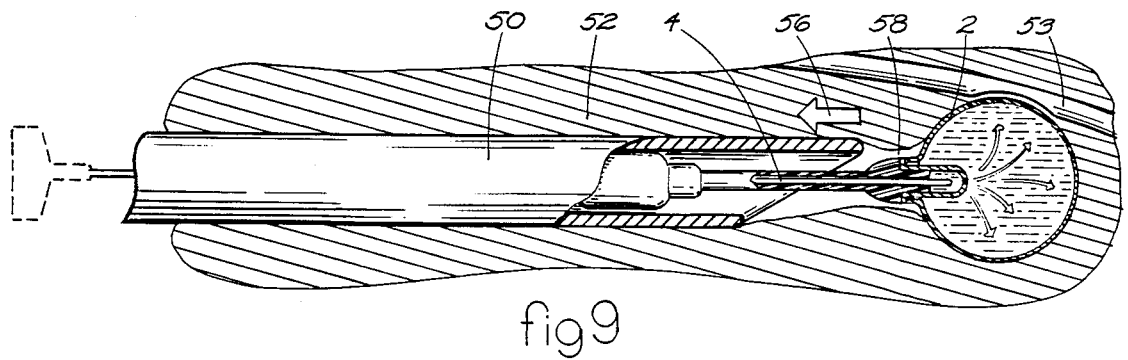

In FIG. 9, the outer trocar tube 50 is retracted slightly (in the direction of the reference arrow 56) through the channel or tunnel 58 which has been pierced through the patient's periurethral tissues 52. The physician then grasps and pushes against the proximal end (not shown) of cannule 4 to move the uninflated occlusion balloon 2 outwardly past the cutting surface of outer trocar tube 50 and into the channel 58 in proximity to the patient's urethra 53.

A hypodermic needle (shown in phantom), which may be filled with suspended TEFLON particles, spheres, radio opaque isotonic fluid, isotonic saline solution, or the like, is placed in communication with the proximal end of cannula 4, and a measured supply of such fluid or suspended particles is expulsed from the syringe for delivery to the occlusion balloon 2 by way of cannula 4. Accordingly, the occlusion balloon 2 is percutaneously infused with and inflated by a regulated volume of material according to the tissue requirements of the patient to increase both the localized tissue volume adjacent the urethra 53 and the passive occlusive pressure applied thereto to restore a patient to urinary continence. By virtue of the present invention, the occlusion balloon 2 may be precisely infused with the minimal volume of liquid or solid particulate suspension necessary to achieve continence of the urethral tissues 52 whereby to reduce the possibility of impeding the flow of blood through the urethra as a consequence of ischemia.

Figure 10:
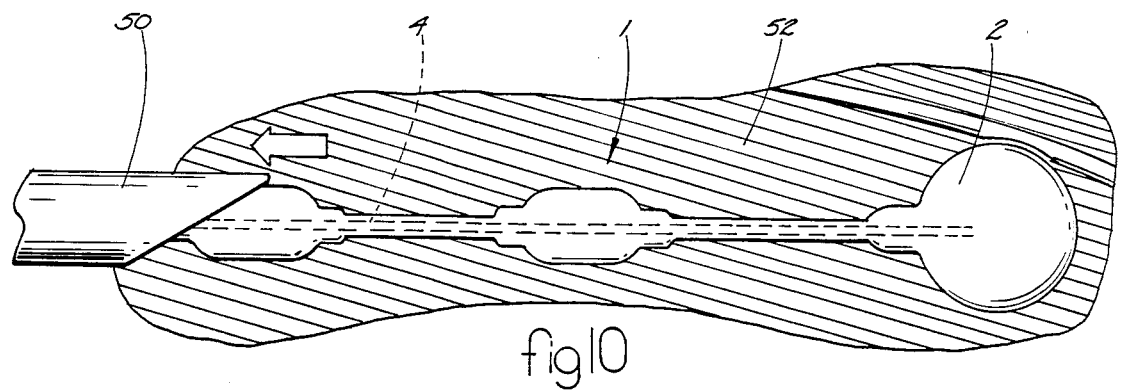

In FIG. 10, after inflation of the occlusion balloon 2, the physician pulls back on and remove the outer trocar tube 50 from the urethral tissues 52. Next, the physician grasps the proximal end of cannula 4 and withdraws the cannula from the sphincteric system 1.

Figure 11:
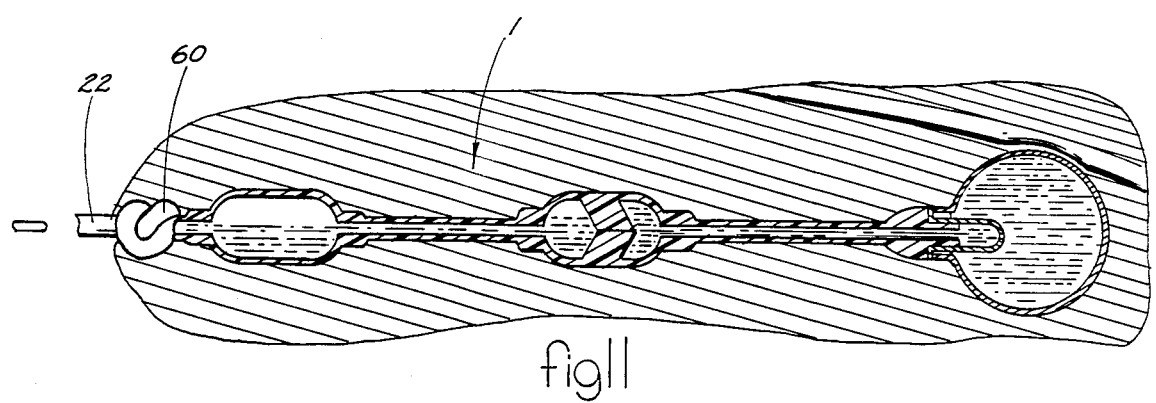

In FIG. 11, the physician clamps the proximal tubing section 22 of sphincteric system 1. With tubing section 22 clamped, the O-ring (designated 24 in FIG. 1) is removed. The tubing section 22 is then tied into a suitable surgical knot 60, whereby to seal off the proximal end of sphincteric system 1 and prevent any leakage therepast. The sphincteric system 1 is now fully implanted, and the physician may close the incision created when the outer trocar tube is removed from the patient's tissues.

Figure 12:
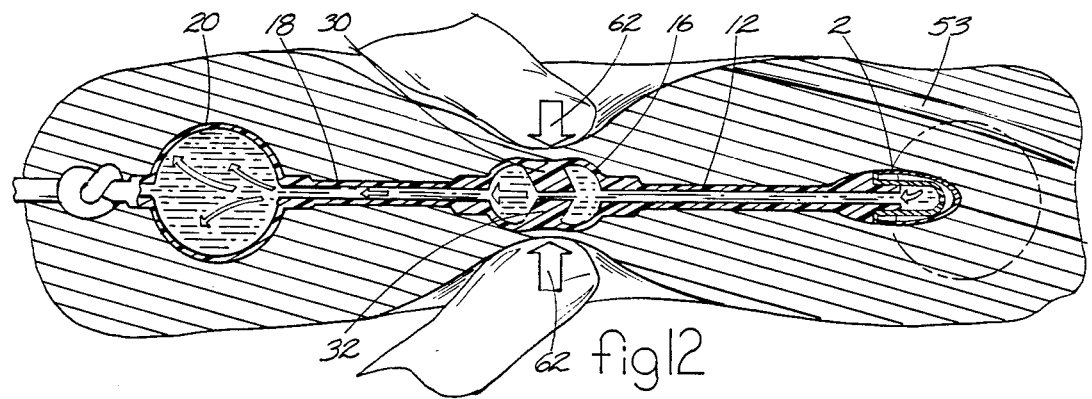
FIGS. 12 and 13 represent steps by which the patient may actively adjust the present sphincteric system after implantation for deflating and reinflating the balloon.

In FIG. 12, after the implant surgery has been completed, the patient may wish to manually reduce the passive occlusive pressure generated by an inflated occlusion balloon 2. To enable the patient to accomplish the foregoing, the check valve 16 and accumulator 20 are subcutaneously implanted at a manually accessible, palpable or loose skin area. Initially, the patient tactily locates the check valve 16 at the loose skin area of his anatomy. By using his thumb and forefinger to apply equal and opposite axial, compressive forces to the opposing pressure surfaces of check valve 16 (in the directions of reference arrow 62) the patient causes the lobes 30 and 32 to separate and, thereby, creates an opening therebetween. Fluid or suspended particles are transferred from the occlusion balloon 2 to the accumulator 20, via distal and medial tubing sections 12 and 18 and check valve 16, whereupon the balloon 2 is deflated to its normally biased condition. The infusion of fluid or particles from balloon 2 to accumulator 20 correspondingly causes the accumulator to fill.

Figure 13:
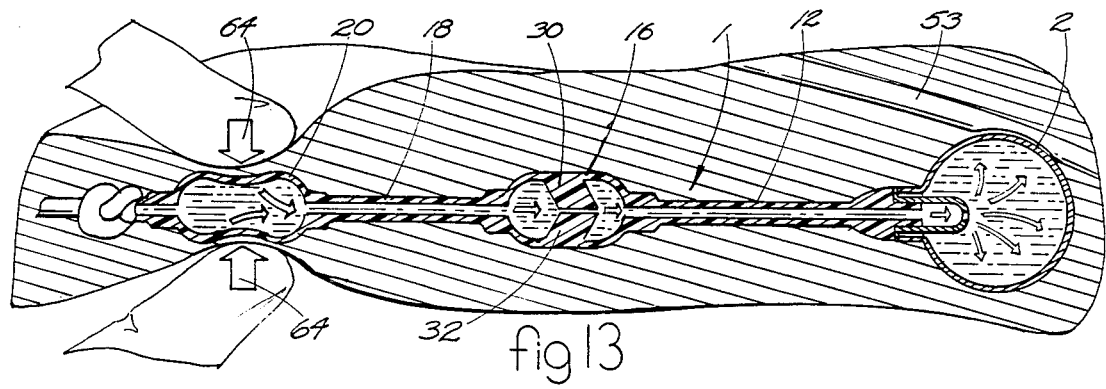

At a later time, and referring now to FIG. 13, the patient may wish to return to continence. In this case, the patient tactily locates accumulator 20 at the loose skin area of his anatomy. By using his thumb and forefinger to apply equal and opposite axial, compressive forces to the accumulator 20 (in the direction of reference arrows 64), fluid is supplied, by hydrostatic pressure, from accumulator 20, past the lobes 30 and 32 of check valve 16, and into occlusion balloon 2 via medial and distal tubing sections 18 and 12. Accumulator 20 is emptied, and the balloon 2 is reinflated, whereby to increase both the localized tissue volume adjacent the urethra 53 and the corresponding passive occlusive pressure generated thereby to enable the patient to regain urinary continence.

Figure 14:
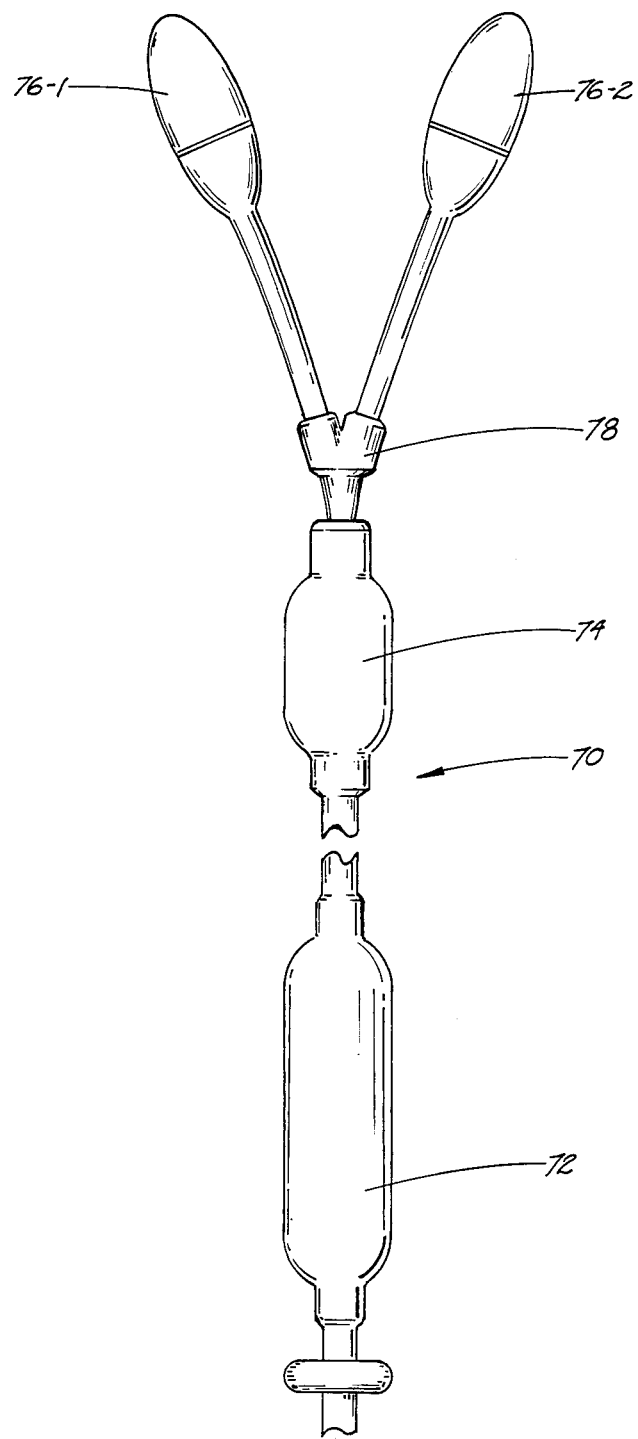
FIG. 14 shows a sphincteric system which forms an alternate embodiment of the present invention.

FIG. 14 of the drawings shows an alternate sphincteric system 70. Sphincteric system 70 is similar to the system 1 illustrated in FIG. 1, including an accumulator 72 and a check valve 74. However, sphincteric system 70 includes a pair of occlusion balloons 76-1 and 76-2 and a suitable (e.g. Y-shaped connector 78 to couple the balloons to the check valve 74. Sphincteric system 70 is preferable when it is desirable to simultaneously implant a pair of occlusion balloons 76-1 and 76-2 on opposite sides of the patient's urethra when maximized occlusive pressure is required to return the patient to continence.

It will be apparent that while a preferred embodiment of the invention has been shown and described, various modifications and changes may be made without departing from the true spirit and scope of the invention. Having thus set forth a preferred embodiment of the invention,

What is claimed is:

1. An implantable, manually adjustable sphincteric system to control the flow of matter through a passage within the human anatomy for the treatment of incontinence, said sphincteric system comprising:

an inflatable/deflatable containment membrane comprising an expandable balloon being in a normally uninflated condition and adapted to be inflated with a supply of material to thereby increase the local tissue density proximally to said passage for correspondingly increasing the passive occlusive pressure applied to said passage;

accumulator means communicating with said balloon to receive material from said balloon when said balloon is deflated and to return said material to said balloon for reinflating said balloon; and flow control means located between said balloon and said accumulator means to control the transfer of material therebetween, said flow control means having passage means being normally biased in a closed condition to prevent the transfer of material therethrough, and force transmitting surface means positioned around said passage means, said passage means being opened, against the normal bias thereof, to permit the transfer of material between said accumulator means and said inflatable balloon in response to a compressive force that is applied to either of said accumulator means, for inflating said balloon, or to said force transmitting surface means, for deflating said balloon.

2. The sphincteric system recited in claim 1, wherein said flow control means is a check valve.

3. The sphincteric system recited in claim 1, wherein said accumulator means is an inflatable manually actuatable reservoir that is implanted at a palpable subcutaneous location, the manual application of equal and opposite compressive forces to said reservoir causing material to be supplied, under pressure, to said balloon via said flow control means.

4. The sphincteric system recited in claim 1, further comprising an elongated, removable cannula passing through said accumulator means and said flow control means and extending between the interior of said balloon in the uninflated condition and a source of said material, said cannula delivering material from said source to said balloon to inflate said balloon, said cannula being removed from said balloon after said balloon has been inflated.

5. The sphincteric system recited in claim 4, further comprising a safety shield located at the interior of said balloon and preventing said cannula from penetrating said balloon when material is being delivered to said balloon by way of said cannula.

6. The sphincteric system recited in claim 5, further comprising at least one delivery port extending through said safety shield to permit the delivery of material from said cannula to the interior of said balloon.

7. The sphincteric system recited in claim 1, further comprising an additional inflatable/deflatable containment membrane comprising an expandable balloon being in a normally uninflated condition, and coupling means for coupling said containment ballons together in common communication with said accumulator means and said flow control means, so that material can be transferred between said accumulator means and said balloons via said flow control means and said coupling means.

8. The sphincteric system recited in claim 1, wherein the passage means of said flow control means comprises a normally closed slit through which material may be transferred between said accumulator means and said balloon when said slit is opened, and the force transmitting surface means of said flow control means comprises a pair of surfaces transversely aligned with said slit and located at opposite ends thereof, such that the application of equal and opposite compressive forces to said pair of force transmitting surfaces causes said slit to open and permit material to be transferred from said balloon to said accumulator means to cauase a deflation of said balloon.

9. The sphincteric system recited in claim 1, wherein the passage means of said flow control means comprises at least one pair of normally closed slits being axially aligned with and spaced from one another so that the material can be transferred between said accumulator means and said balloon when said slits are opened, and the force transmitting surface means of said flow control means comprises a pair of surfaces transversely aligned with said pair of slits and located at opposite ends thereof, such that the application of equal and opposite compressive forces to said pair of force transmitting surfaces causes said pair of slits to open and permit material to be transferred from said balloon to said accumulator means to cause a deflation of said balloon.

10. The sphincteric system recited in claim 1, wherein the passage means of said flow control means comprises a plurality of pairs of normally closed slits, each of the slits of a pair thereof being axially aligned with and spaced from one another so that material can be transferred between said accumulator means and said balloon when at least one pair of slits are opened, and the force transmitting surface means of said flow control means comprises a corresponding plurality of pairs of surfaces, each pair of force transmitting surfaces being transversely aligned with a respective pair of said slits and located at opposite ends thereof, such that the application of equal and opposite compressive forces to one of the plurality of pairs of force transmitting surfaces causes a corresponding one of said plurality of pairs of slits to open and permit material to be transferred from said balloon to said accumulator means to cause a deflation of said balloon.

11. The sphincteric system recited in claim 10, wherein said pairs of force transmitting surfaces are located around the periphery of said flow control means to surround said pairs of slits.

12. An implantable sphincteric system to be implanted to control the flow of matter through a passage within the human anatomy for the treatment of incontinence, said sphincteric system comprising:

an inflatable membrane to be inflated with a supply of fluid to increase the local tissue density proximally to said passage for correspondingly increasing the occlusive pressure applied to said passage;

fluid reservoir means communicating with said membrane to supply fluid to and receive fluid from said membrane;

check valve means located between said membrane and said reservoir means to control the flow of fluid therebetween; and hollow cannula means communicating with a source of fluid at one end thereof and adapted to be removably inserted through said reservoir means and said check valve means so as to communicate at the opposite end thereof with said membrane to inflate said membrane with fluid from said source, said cannula means being removable from said system after said membrane has been inflated.

13. A method for implanting a sphincteric system to control the flow of matter through a passage within the human anatomy for treating incontinence, said system including an inflatable membrane to be inflated with a supply of material to increase the occlusive pressure applied to said passage, a reservoir communicating with said membrane to supply material to and receive material from said passage, and a flow control valve located between said membrane and said reservoir to control the flow of material therebetween, said method for implanting including the steps of:

piercing the tissues of a patient with a hollow trocar for establishing a channel through said tissues;

inserting a hollow cannula through the reservoir and flow control valve of said sphincteric system and into communication with said membrane;

locating said system within said trocar;

urging said system outwardly of said trocar until said membrane is positioned in proximity to said passage;

inflating said membrane via said cannula with a supply of material from a source thereof;

removing the trocar from the patient's tissues; and removing the cannula from the sphincteric system leaving said system implanted within the patient's tissues.

14. The method recited in claim 13, including the additional steps of inserting a non-coring rod through said hollow trocar before the step of piercing the patient's tissues; and removing said non-coring rod from said trocar after the tissues have been pierced and the channel established.

15. The method recited in claim 13, including the additional step of locating said hollow cannula at the interior of said inflatable membrane before the step of inflating said membrane via said cannula.

16. The method recited in claim 13, including the additional step of positioning said sphincteric system such that said flow control valve and said reservoir are located at manually accessible subcultaneous areas of the patient.

17. The method recited in claim 13, including the additional step of clamping said sphincteric system to prevent the escape of material therefrom after the steps of removing said trocar and removing said cannula.

18. The method recited in claim 13, including the additional step of forming said reservoir and said flow control valve from a flexible material, such that said reservoir and said flow control valve may be controlled by the application of manually generated compressive forces thereto.

* * * * *